United States Patent
Astarita

(10) Patent No.: US 10,410,846 B2
(45) Date of Patent: *Sep. 10, 2019

(54) MOLECULAR DIAGNOSTICS IN PERSONALIZED DERMATOLOGY, DERMATOPATHOLOGY AND COSMETICS

(71) Applicant: Waters Technologies Corporation, Milford, MA (US)

(72) Inventor: Giuseppe Astarita, Hopkinton, MA (US)

(73) Assignee: WATERS TECHNOLOGIES CORPORATION, Milford, MA (US)

(*) Notice: Subject to any disclaimer, the term of this patent is extended or adjusted under 35 U.S.C. 154(b) by 0 days.

This patent is subject to a terminal disclaimer.

(21) Appl. No.: 15/880,748

(22) Filed: Jan. 26, 2018

(65) Prior Publication Data

US 2018/0190479 A1 Jul. 5, 2018

Related U.S. Application Data

(63) Continuation of application No. 15/176,822, filed on Jun. 8, 2016, now Pat. No. 9,881,777.

(Continued)

(51) Int. Cl.
*H01J 49/00* (2006.01)
*G01N 33/483* (2006.01)
(Continued)

(52) U.S. Cl.
CPC .......... *H01J 49/0031* (2013.01); *A23L 33/10* (2016.08); *G01N 33/4833* (2013.01);
(Continued)

(58) Field of Classification Search
CPC .... H01J 49/04; H01J 49/0409; H01J 49/0418; H01J 49/0459; H01J 49/0463; H01J 49/10; H01J 49/16
(Continued)

(56) References Cited

U.S. PATENT DOCUMENTS

| 6,516,245 B1 | 2/2003 | Dirksing et al. |
| 6,586,727 B2 | 7/2003 | Bateman et al. |

(Continued)

FOREIGN PATENT DOCUMENTS

| WO | 2006092689 A1 | 9/2006 |
| WO | 2013013864 A1 | 1/2013 |

OTHER PUBLICATIONS

UKIPO Combined Search and Examination Report issued for Application No. GB1609839.4, dated Mar. 22, 2017.

(Continued)

*Primary Examiner* — Nicole M Ippolito
(74) *Attorney, Agent, or Firm* — Womble Bond Dickinson (US) LLP; Deborah M. Vernon; Rebecca N. Barnes

(57) ABSTRACT

The present disclosure relates generally to methods and apparatus for determining components and associated conditions in a dermatological sample, and preparing personalized cosmetics or treatments. In particular, the present disclosure relates to the use of surface desorption ionization-mass spectrometry methods and apparatus to assay dermatological samples. The method and apparatus can allow real time analysis of sample molecules, such as in skin and hair, for molecular diagnostics in dermatology, dermatopathology and the preparation of personalized cosmetics.

19 Claims, 7 Drawing Sheets

Related U.S. Application Data

(60) Provisional application No. 62/172,989, filed on Jun. 9, 2015.

(51) Int. Cl.
  *A23L 33/10* (2016.01)
  *G01N 27/62* (2006.01)
  *G01N 30/72* (2006.01)

(52) U.S. Cl.
  CPC ....... H01J 49/0036 (2013.01); *A23V 2002/00* (2013.01); *G01N 27/62* (2013.01); *G01N 30/72* (2013.01)

(58) Field of Classification Search
  USPC .................................. 250/281, 282, 283, 288
  See application file for complete search history.

(56) References Cited

U.S. PATENT DOCUMENTS

| | | | |
|---|---|---|---|
| 6,717,130 | B2 | 4/2004 | Bateman et al. |
| 8,471,199 | B1 | 6/2013 | Doroshenko et al. |
| 9,881,777 | B2* | 1/2018 | Astarita ............. H01J 49/0031 |
| 2010/0261215 | A1 | 10/2010 | Mehul et al. |
| 2012/0156712 | A1 | 6/2012 | Takats |
| 2013/0288355 | A1 | 10/2013 | DeWitte et al. |
| 2013/0299688 | A1 | 11/2013 | Balogh et al. |
| 2015/0176072 | A1* | 6/2015 | Wang .................. C12Q 1/6886 506/9 |
| 2019/0033313 | A1* | 1/2019 | Gravenstein ....... G01N 33/5743 |

OTHER PUBLICATIONS

Mess A. et al., "A novel sampling method for identification of endogenous skin surface compounds of DART-MS and MALDI-MS" Talanta, vol. 103, 2013.

Park, H.M. et al., "Direct Analysis in Real Time mass Spectrometry (DART-MS) Analysis of Skin Metabolome Changes in the Ultraviolet B-Induced Mice." Biomolecules & Therapeutics, vol. 21 (6), 2013. pp. 470-475.

Schweiger D. et al., "Efficacy of a New Tonic Containing Urea, Lactate, Polidocarml, and Glycyrrhiza infinita Root Extract in the Treatment of a Dry, Itchy, and Subclinically inflamed Scalp" Journal of Pharmacological and biophysical research. vol. 26(2), 2013 pp. 108-118.

Nordstrom, Katrina M., et al., "Characterization of Wax Esters, Triglycerides, and Free Fatty Acids of Follicular Casts", The Journal of Investigative Dermatology, Jun. 1986, vol. 86, No. 6, pp. 700-705.

O'Neill, Hugh J., et al., "Analysis of Fatty Acid and Alcoholic Components of Sebaceous Lipid Types", Journal of Chromatographic Science, Jan. 1976, vol. 14, No. 1, pp. 28-36.

Sullivan, Benjamin D., et al., "Complete Androgen Insensitivity Syndrome, Effect on Human on Meibomlan Gland Secretions", Archives of Opthalmology, Dec. 2002, vol. 120, pp. 1689-1699.

Cornellson, C.D., et al. "MALDI-MS Redox Lipidomics Applied to Human Hair: A First Look", International Journal of Trichology, 2011, vol. 3, Issue 1, pp. 25-27.

Duvel, L., et al., "Analysis of Hair Lipids and Tensile Properties as a Function of Distance from Scalp", International Journal of Cosmetic Science, 2005, vol. 27, pp. 193-197.

Sulek, Karolina, et al., "Hair Metabolomics: Identification of Fetal Compromise Provides Proof of Concept for Biomarker Discovery", Theranostics, 2014, vol. 4, Issue 9, pp. 953-959.

Katona et al. "Intact skin analysis by desorption electrospray ionization mass spectrometry." Analyst. 136(2011): 835-840.

Michael-Jubeli et al. "High-termperature gas chromatography-mass spectrometry for skin surface lipids profiling." J. Lipid Res. 52(2011): 143-151.

Examination Report issued in corresponding GB Application No. 1814271.1 dated Jun. 10, 2019.

\* cited by examiner

MOLECULAR DIAGNOSTICS IN PERSONALIZED DERMATOLOGY, DERMATOPATHOLOGY AND COSMETICS

CROSS-REFERENCE TO RELATED APPLICATIONS

This application is a continuation application of U.S. patent application Ser. No. 15/176,822, filed on Jun. 8, 2016, now U.S. Pat. No. 9,881,177; U.S. patent application Ser. No. 15/176,822 claims the benefit of and priority to U.S. Provisional Patent Application No. 62/172,989, filed on Jun. 9, 2015. Each of the foregoing applications is incorporated by reference in its entirety.

TECHNICAL FIELD

The present disclosure relates generally to methods and apparatus for determining components and associated conditions in a dermatological sample, and preparing personalized cosmetics or treatments. In particular, the present disclosure relates to the use of surface desorption ionization-mass spectrometry methods and apparatus to assay dermatological samples. The method and apparatus can allow real time analysis of sample molecules, such as in skin and hair, for molecular diagnostics in dermatology, dermatopathology and the preparation of personalized cosmetics.

BACKGROUND OF THE INVENTION

Personalized cosmetic products, such as shampoo, skin creams, lipstick, etc. have long been used by customers and patients to enhance their physical health and appearance. Many customers and patients, however, select a personalized product based on their perceived needs or recommendations from other persons. The selection is often not based on the specific chemistry of the customer or patient's anatomy to which the product will be applied or used. As a result, customers and patients do not use personalized products that sufficiently address or otherwise treat, either partially, substantially or completely, their situation or condition.

The chemistry associated with a customer or patient's anatomy, or a cosmetic treatment, formulation, food/diet, dosage form, etc. can be obtained using conventional analytical tools and methodology. But, such conventional tools and methodology is labor intensive and time consuming, and not amenable to a real-time analysis. For example, current test methods include gas chromatography-mass spectrometry (GC-MS). Analysis by GC-MS requires a multi-step procedure for sample preparation, e.g., hydrolysis and derivatization, and a chromatographic separation. Alternatively, liquid chromatography-tandem mass spectrometry (LC-MS) can be used for the direct measurement of various compounds without the need for hydrolysis or derivatization. LC-MS still requires the labor intensive and time consuming chromatographic separation step. Supercritical fluid chromatography-mass spectrometry and other similar techniques can also be used, but these techniques also suffer from the same requirement.

The present disclosure relates to methods and apparatus for screening the chemistry of dermatological and cosmetic related samples which are less time consuming and resource intensive.

SUMMARY OF THE INVENTION

The present disclosure relates generally to methods and apparatus for determining components and associated conditions in a dermatological sample, and preparing personalized cosmetics or treatments. In particular, the present disclosure relates to the use of surface desorption ionization-mass spectrometry methods and apparatus to assay dermatological samples. The method and apparatus can allow real time analysis of sample molecules, such as in skin and hair, for molecular diagnostics in dermatology, dermatopathology and the preparation of personalized cosmetics.

In one embodiment, the present disclosure relates to a method of analyzing a dermatological sample including generating sample ions from the dermatological sample using a surface desorption ionization source, receiving the ions into a mass spectrometer, identifying dermatological related compound(s) in the sample, comparing the identified dermatological related compound(s) in the sample to one or more known dermatological profiles, and identifying a condition, e.g., deficiency, in the dermatological sample. The sample can be skin, hair, a secretion, etc. The sample can be obtained from a subject, such as a biopsy, or the subject can be the sample, e.g., in situ analysis. The present disclosure can stratify subject, consumers, customers, patients, etc. into groups for the application of personalized cosmetics or treatments.

In another embodiment, the present disclosure relates to a method of providing a personalized cosmetic product to a customer, consumer, patient, etc. including receiving dermatological data from a dermatological analysis of a sample provided by the customer, obtaining ingredients for producing the personalized cosmetic product, generating a customized cosmetic product formula using the ingredients and dermatological data, and preparing the customized cosmetic product, wherein these steps can be performed in a relatively short period of time, such as less than about 1 hour or 30 minutes. The dermatological data can be obtained or received by generating sample ions from the customer's sample using a surface desorption ionization source, receiving the ions into a mass spectrometer, identifying dermatological related compound(s) in the sample. The dermatological data from the customer can be saved for subsequent use.

In another embodiment, the present disclosure relates to a method of treating a dermatological condition in a subject including determining the dermatological condition in the subject by obtaining a dermatological sample from the subject, generating sample ions from the subject's sample using a surface desorption ionization source, receiving the ions into a mass spectrometer, identifying dermatological related compound(s) in the sample, and administering a cosmetic, supplement, food, diet or a dosage form to the subject to reduce or eliminate the dermatological condition.

The methods and apparatus of the present disclosure provide several advantages over the prior art. The present disclosure can be used for real-time, robust, rapid, in-situ screening and assessing of dermatological and cosmetic related samples. Such assessments can be indicative of health status or the condition of the subject, or the quality of a cosmetic, supplement, food, diet or dosage form. The quick feedback provided by the methods of the present disclosure can assist in dermatological and cosmetic suggestions for treatment, such as during a single visit. By assessing the chemical component profile(s) in dermatological and cosmetic related samples a wide range of conditions or pathologies can be monitored, reduced, treated or prevented. The methods and apparatus can be used to monitor the health status and well-being of both individuals and populations. Personalized products can also be designed to address the personal features of the customers etc. in real-time, without requiring extensive and expensive lab tests. For example, skin conditions can be monitored longitudinally in time and populations can be screened for sign of skin aging and inflammatory skin response, allergies, dryness, and pathologies. The present disclosure can also be performed without an internal standard or pre-calibrations.

BRIEF DESCRIPTION OF THE DRAWINGS

The foregoing and other features and advantages provided by the present disclosure will be more fully understood from the following description of exemplary embodiments when read together with the accompanying drawings, in which:

FIG. 7A shows a close up view of the outside of the instrument. FIG. 7B shows a view of the inside of the instrument.

DETAILED DESCRIPTION

Figure 1:
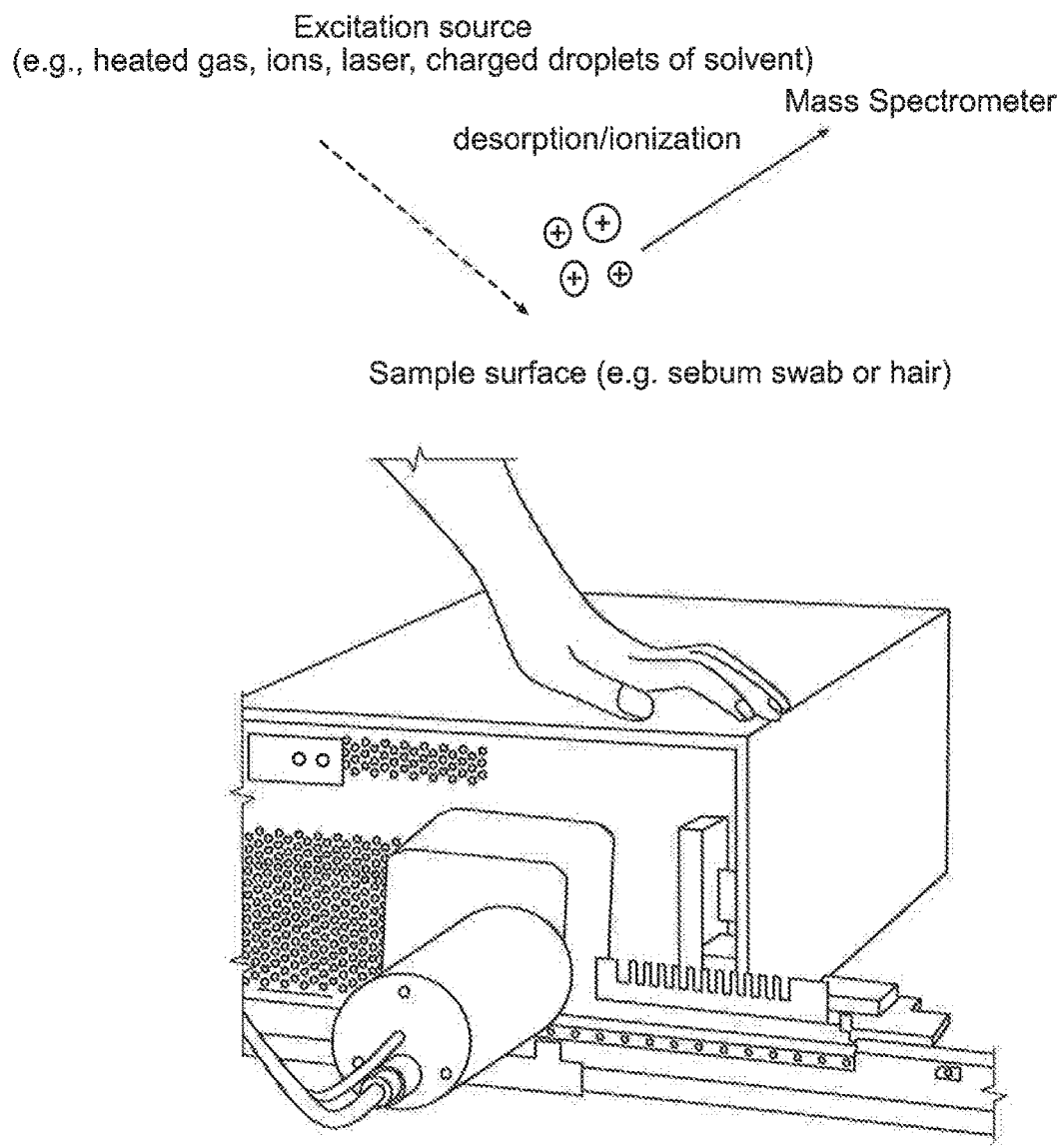
FIG. 1 shows an exemplary illustration of an excitation source incident upon a sample surface which generates samples ions that are introduced to a mass spectrometer for analysis. The excitation source can be heated gas, ions, laser, charged droplets of solvent, etc. The sample can be a sebum swab or a hair sample.
Figure 2:
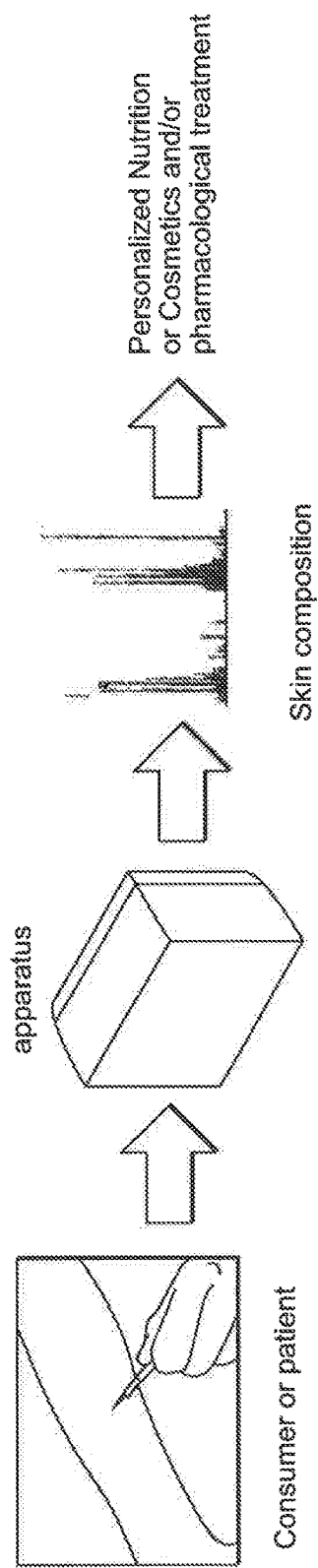
FIG. 2 shows an exemplary overview of the analysis. A sample can be taken from a patient or customer. The sample can be tested or analyzed using an apparatus of the present disclosure. The apparatus can identify (e.g., qualitative and/or quantitative) one or more components in the sample, such as the composition of skin. The results can be analyzed or compared to standards or other metrics to determine a personalized treatment, nutrition, cosmetic and/or pharmacological product for the patient or customer.

The present disclosure relates generally to methods and apparatus for determining components and associated conditions in a dermatological sample, and preparing personalized cosmetics or treatments. In particular, the present disclosure relates to the use of surface desorption ionization-mass spectrometry methods and apparatus to assay dermatological samples. The method and apparatus can allow real time analysis of sample molecules, such as in skin and hair, for molecular diagnostics in dermatology, dermatopathology and the preparation of personalized cosmetics.

As used herein the term "dermatology," "dermatological" and "dermatopathology" refer generally to the study or examination of the skin and subcutis, hair, nails, and the like, and the study of the causes of related conditions or diseases.

In one embodiment, the present disclosure relates to a method of analyzing a dermatological sample including generating sample ions from the dermatological sample using a surface desorption ionization source, receiving the ions into a mass spectrometer, identifying at least one dermatological related compound, or compounds, in the sample, comparing the identified dermatological related compound, or compounds, in the sample to one or more known dermatological profiles, and identifying a condition in the dermatological sample.

The dermatological sample can be any dermatological sample taken from a person or subject (e.g., person, animal, etc.). The sample can be a skin sample, a hair sample, a nail sample, a secretion or extract from a skin, hair or nail sample, or combination thereof. The dermatological sample can be obtained from the person or subject, such as a biopsy or other removal of the skin, hair or nail from the subject. The sample can also be tested, screened or analyzed directly, i.e., wherein the samples ions are generated in situ directly from the subject. In some embodiments, the surface desorption ionization source can be a gentle or soft ionization technique which does not substantially damage or exhaust an in situ dermatological sample. In one embodiment, the sample can be a skin or hair sample from an animal, such as a pet.

The sample can also be a tissue biopsy, sebum, meibum, sweat or combinations thereof. The method of the present disclosure can be applied to volatile, liquid and solid samples, including swabs, hair, hair root, fingers, tissue, sponges, combs, brushes, plates, and skin biopsy of both dermal and epidermal layers of the skin, hair follicles and scalp biopsy and dandruff.

In particular, the present disclosure is related to skin and components of skin. Skin is composed of three primary layers, the stratum corneum, the epidermis, and the dermis. The present disclosure can evaluate all three layer, such as in dermis or epidermis biopsies. The outer layer of the skin, the stratum corneum, primarily functions as a barrier to the external environment preventing water loss and preventing the invasion of microorganisms. Lipids, secreted to the stratum corneum from the sebaceous glands, are the key components in maintaining this barrier.

Sebum, a complex mixture of proteins and lipids, is produced by the sebaceous glands. At maturation, the acinar cells of the sebaceous glands lyse and release sebum into the lumenal duct, from which the sebum is secreted. Squalene, cholesterol, cholesterol esters, wax esters, and triglycerides are the primary lipids found in human sebum. Wax esters and squalene are unique to sebum in that they are not synthesized by other cells in the body. During passage of sebum to the skin surface, bacterial enzymes hydrolyze some of the triglycerides, so that the lipid mixture reaching the skin surface also contains free fatty acids and small amounts of mono- and diglycerides.

The meibonian gland is a sebaceous gland that produces the tear film's lipid layer (meibum). Polar and non-polar lipids are present in the meibum. The non-polar lipids include wax and sterol esters and hydrocarbons, while the main polar lipid components are phospholipids, sphingolipids and triglycerides.

Figure 6:
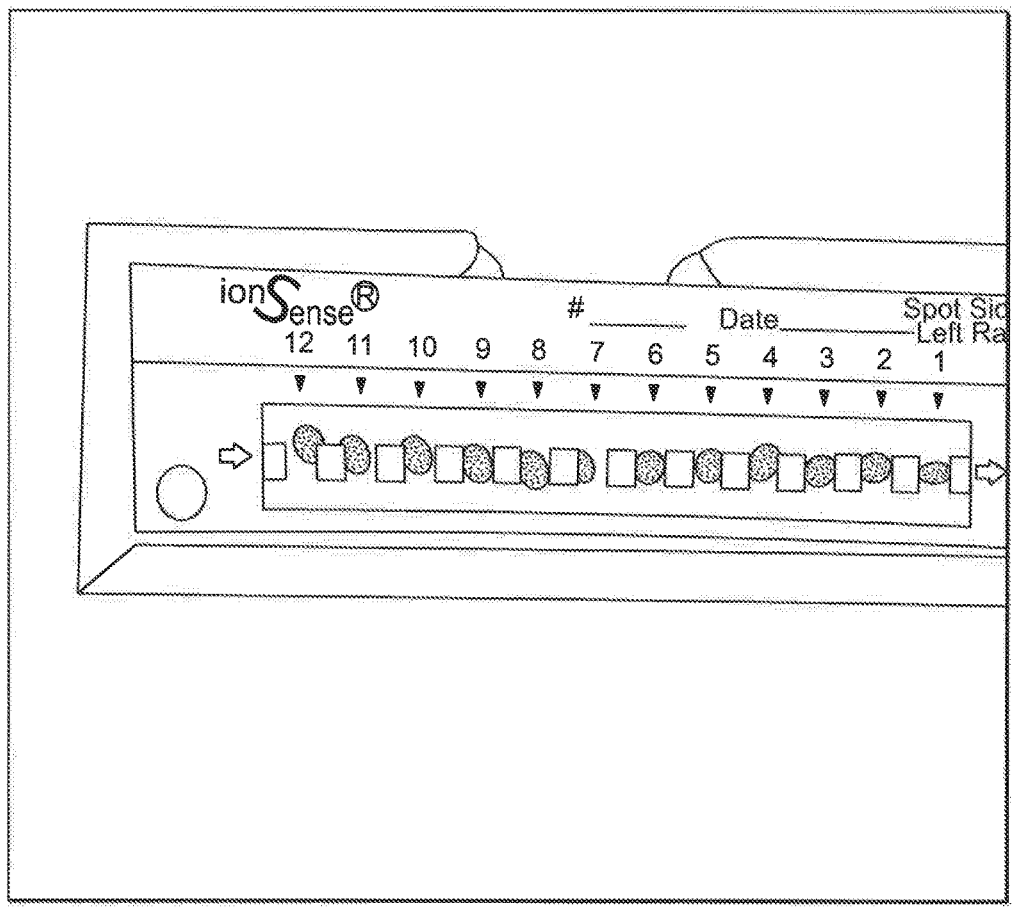
FIG. 6 shows an exemplary embodiment of the present disclosure including a sample preparation device for use with direct-analysis in real time (i.e., DART®) and a single quadrupole mass spectrometer. For example, skin or hair samples can be placed on the mesh sample areas (indicated by the arrows).

The sample can be analyzed with no substantial preparation, such as filtering, extraction, isolation or combinations thereof. The sample can be analyzed neat, or with no sample preparation. For example, a sample or samples can be swiped on glass capillaries and held, placed or otherwise introduced to the ionization source, e.g., held in a metastable gas beam between the direct analysis in real time ion source and a mass spectrometer detector. See FIG. 6 for an exemplary sample mesh capable of holding the sample in the ionization source. In one embodiment, the sample preparation is simple such that the sample can be a biological sample, e.g., skin or hair sample on a slide or grid.

The sample can also be associated with a cosmetic or other treatment dosage form to treat a condition or imbalance. The dosage form can be in any form, e.g., tablet, capsule, pill, film, liquid, etc. Depending on the dosage form, the sample can be prepared by neat or by altering the dosage form to access the sample. For example, the sample can be a cosmetic containing encapsulated dosages of fatty acids and UV A and UV B blockers. The sample preparation can include removing a portion of the contents from inside the encapsulation.

The sample ions can be generated using any desorption ionization (DI) source or technique capable of effectively sampling analytes of interest, or classes of analytes of interest, from a sample for introduction into a mass spectrometer. The desorption ionization source or technique can also be any capable of real-time, rapid in-situ testing of solid or liquid samples. In one embodiment, the desorption ionization source is a surface desorption ionization source or technique.

In desorption ionization, the ionization process can begin by irradiating, or otherwise exposing, a defined area or spot on a sample, e.g., solid sample, using a focused energy source. The energy source can be an excitatory beam such as a laser, ions, charged, solvent droplets or heated gas containing metastable ions. Upon impact, the sample's surface releases a vapor of ionized molecules that can be directed into a mass spectrometer. Alternatively, acoustic or thermal desorption can initiate the ionization process.

In one embodiment, the analysis of dermatological samples using a surface desorption ionization-mass spectrometry system is provided. Dermatological samples are particularly suited for surface desorption ionization because they contain many components, such as metabolites, lipid, fatty acids, etc. that can be in high abundance ionize well in negative mode under DI conditions.

The surface desorption ionization source can operate by a technique selected from the group consisting of electrospray ionization, nano-electrospray ionization, matrix-assisted assisted laser desorption ionization, atmospheric pressure chemical ionization, desorption electrospray ionization, atmospheric pressure dielectric barrier discharge ionization, atmospheric pressure low temperature plasma desorption ionization, laser-assisted electrospray ionization, and electrospray-assisted laser desorption ionization.

In particular, the surface desorption ionization source can operate by a technique selected from the group consisting of atmospheric solid analysis probe (i.e., ASAP), direct analysis in real time (DART®), rapid evaporative ionization mass spectrometry (REIMS), desorption electrospray ionization (DESI), matrix assisted laser desorption ionization (MALDI), nanostructure and initiated mass spectrometry (NIMS).

The desorption ionization source can small and have a small footprint. The desorption ionization source can also be suitable or compatible with ambient mass spectrometry, e.g., a mass spectrometer operating at or near atmospheric pressure. In one embodiment, the desorption ionization source or technique is DART®, ASAP, REIMS or DESI. These ionization sources can be small and compatible with ambient mass spectrometry.

Direct Analysis in Real Time is an atmospheric pressure ion source that can instantaneously ionizes gases, liquids or solids in open air under ambient conditions. It is an ambient ionization technique that does not require sample preparation, so solid or liquid materials can be analyzed by mass spectrometry in their native state. Ionization can take place directly on the sample surface. Liquids can be analyzed by, for example, dipping an object (such as a glass rod) into the liquid sample and then presenting it to the DART® ion source. Vapors can be introduced directly into the DART® gas stream.

Figure 3:
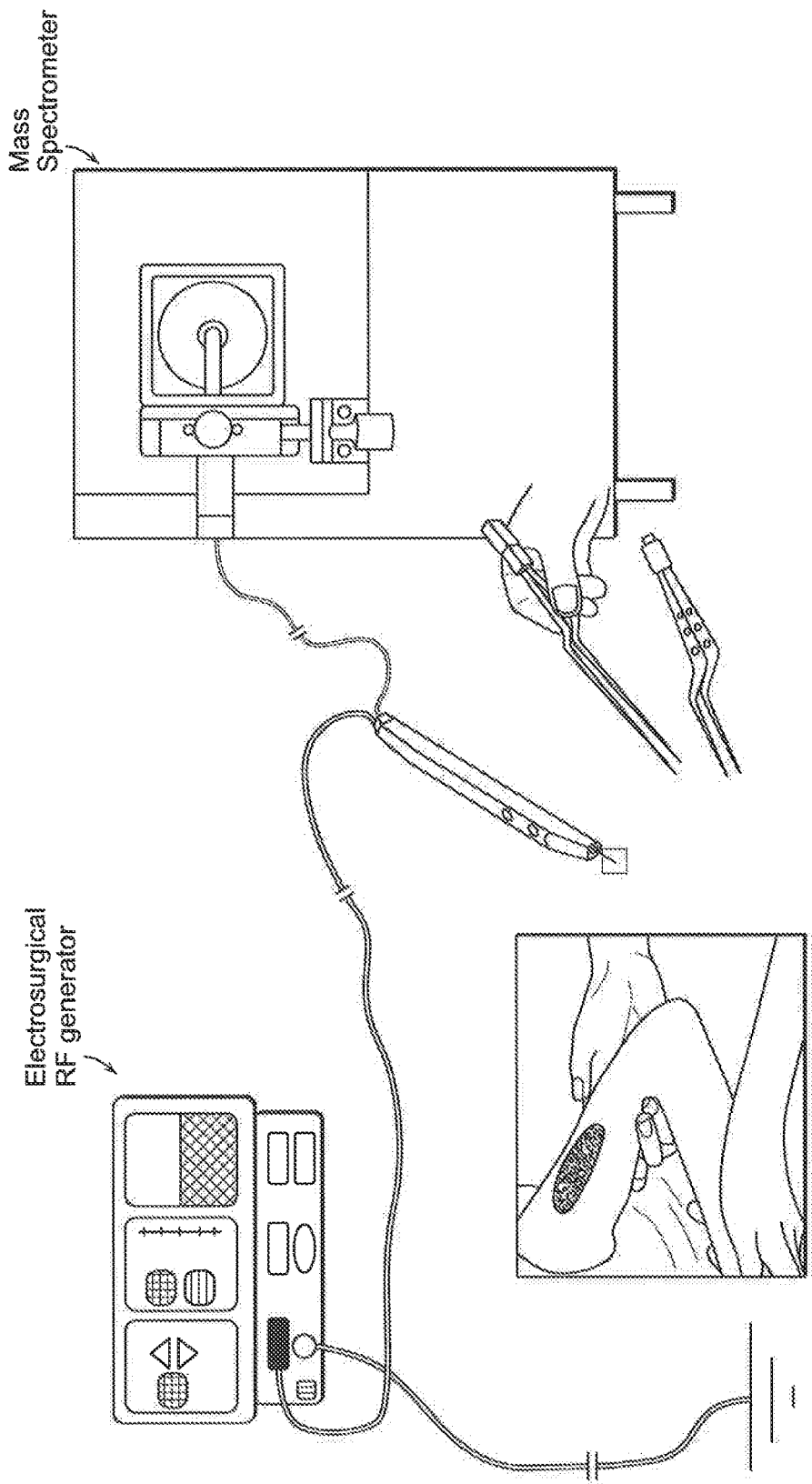
FIG. 3 shows an exemplary embodiment of the present disclosure including REIMS-mass spectrometry for a dermatological assessment of a subject. A noncancerous disorder of pigment-producing skin cells, commonly called birth marks or moles, can be tested in situ.
Figure 4:
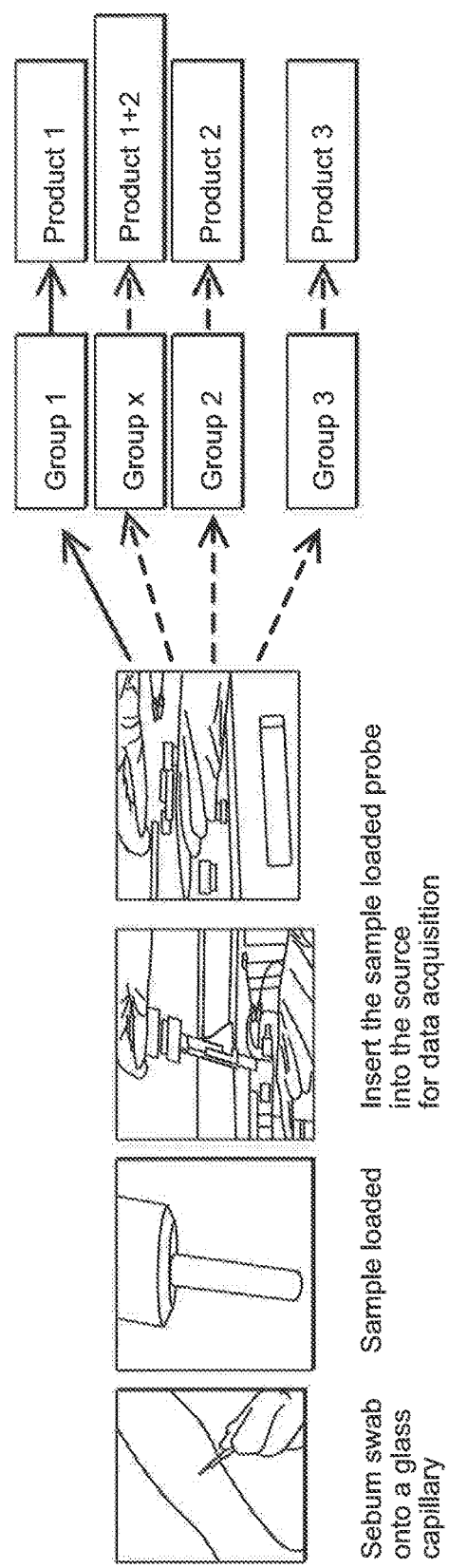
FIG. 4 shows an exemplary embodiment of the present disclosure including ASAP-mass spectrometry for a dermatological assessment of a subject. A sebum swab can be taken onto a glass capillary. The sample can be loaded into a probe and the probe inserted into the ASAP source. Based on preselected markers, the sample can be classified or stratified according to predetermined groups. Personalized products, or mixtures of personalized products, can then be provided.

Atmospheric Solids Analysis Probe is an atmospheric pressure ion source that can directly analyze samples using an atmospheric pressure ionization (API) source. The ASAP probe can analyze solid, liquid, tissue, or material samples. In ASAP, vaporization of a sample can occur when it is exposed to a hot desolvation gas, e.g., nitrogen, from an probe, e.g., an electrospray ionization or atmospheric pressure chemical ionization probe. FIG. 3 shows an embodiment of the apparatus having ASAP and a mass spectrometer. Both DART® and ASAP are similar ionization techniques. ASAP can involve increasing temperature to effect ionization, whereas DART® can involve increasing heated, blown gas to effect ionization.

Rapid Evaporative Ionization Mass Spectrometry (REIMS) is an ionization technique that can be used as a source for direct analysis of samples by mass spectrometry. REIMS is an atmospheric pressure ion source that can ionize gases, liquids or solids in open air under ambient conditions. The REIMS ionization source can be a probe, e.g., electronic scalpel or tweezers to burn and evaporate ions, that can be used to remotely test the samples. See U.S. Patent Publication No. 2012/0156712, the disclosure of which is incorporated herein in its entirety.

Desorption electrospray ionization (DESI) is an ambient ionization technique that can be used in mass spectrometry for chemical analysis. It is an atmospheric pressure ion source that ionizes gases, liquids and solids in open air under ambient conditions. DESI is a combination of electrospray (ESI) and desorption (DI) ionization methods. Ionization can take place by directing an electrically charged mist to a sample surface. The electrospray mist can be attracted to the surface by applying a voltage on the sample or sample holder. After ionization, the ions can travel through air into the atmospheric pressure interface which can be connected to a mass spectrometer.

Thermal desorption ionization can be used as the ionization mechanism. The sample, and biological components, can be exposed to different temperatures to induce ionization. See U.S. Patent Publication No. 2013/0299688, the disclosure of which is incorporated herein in its entirety.

In some embodiments, the energy or temperature of the ionization source may not be sufficiently high to efficiently ionize a representative sample. For example, the sample may contain components having different properties, such as different volatilities. At a certain energy level or temperature, some components may be ionized more readily than others, which can create a bias in the ratio at that energy level or temperature. In one embodiment, the present disclosure includes a step of determining a sufficient energy level (e.g., temperature in thermal desorption) to ionize a representative sample of all components, analytes of interest, or classes of analytes of interest. For example, the energy level can be tested at increasing values until the intensities or ratio of intensities for the analytes of interest stabilize at a constant value indicative of a representative sampling of analytes.

The method can also be robust such that the sampling does not exhaust the components, analytes of interest or classes of analytes of interest, e.g., metabolites, lipids, fatty acids, etc., in the sample. The ionization process can involve a short, e.g., less than about 10 seconds, 9, 8, 7, 6, 5, 4, 3, 2, 1, 0.5, 0.2 or about 0.1 seconds, exposure of the ionization source to the sample. These values can be used to define a range, such as about 2 to about 0.2 seconds.

The sample ions can be received or introduced to a mass spectrometer by any means or technique capable of effectively introducing ions into a mass spectrometer that can allow for real-time, rapid in-situ testing of solid or liquid samples. For example, the ions can be introduced under ambient conditions.

The mass spectrometer can be any mass spectrometer capable of receiving the sample ions, of producing accurate mass measurements, and of identifying sample analytes of interest. The mass spectrometer can be a quadrupole mass spectrometer, portable ion trap mass spectrometer, time of flight mass spectrometer, Fourier transform ion cyclotron resonance mass spectrometry, orbi trap or ion mobility spectrometer. For example, the mass spectrometer can be a single quadrupole QDa® detector, e.g., a DART®-QDa® or a REIMS-QDa®.

The analytes of interest can be analyzed by selection reaction monitoring in a quadrupole instrument. Selection reaction monitor involves pre-selection of a list of ions of interest or extracted from full scan accurate mass spectra, in which no ion is preselected but the quadrupole is scanned along all the mass range selected (e.g., 50-100 m/z).

The mass spectrometer can be operated in positive or negative mode. In one embodiment, the mass spectrometer is operated in negative mode under desorption ionization conditions. Metabolites, lipids, fatty acid, etc. can ionize particularly well in negative mode. The coupling of a mass spectrometer, e.g., a single quadrupole device, with desorption ionization can also allow for the direct analysis of metabolites, lipids, fatty acid, etc. as a function of peak intensity or as a ratio between peaks or groups of peaks. The ratio of metabolites, lipids, fatty acid, etc. can be used to normalize for variation in instrument settings and sampling. For example, a variation in intensity of one fatty acid(s) is compensated by an equivalent variation in another fatty acid(s). Their ratio can be used to normalize for difference between samples.

The amount or relative amount (e.g., ratio) of analytes of interest, or classes of analytes of interest, can be calculated from the mass spectrometry results, such as the intensity of the peaks. The calculations can be made with or without the use of an internal standard. For example, the relative amount can be a simple ratio of the intensities of the mass signals. The use of internal standard(s) can provide semi-quantification after correcting for any isotopic contribution to the signal. For example, internal standards can be used to normalize the concentration of the components in the samples to obtain a more quantitative measurement.

In some embodiments, the analytes of interest, e.g., metabolites, lipids, fatty acid, etc., can be derivatized or tagged before DI-MS analysis. MS/MS analysis of the tagged analytes can then be performed. For example, charge-reversal derivatization of fatty acids can be performed wherein the carboxylic acids are converted into cationic derivatives with quaternary amines. Detection by ESI can be improved. Also, electron capture atmospheric pressure chemical ionization can be performed on analytes that have been tagged with an electron-capturing group such as the pentafluorobenzyl moiety. Detection by APCI can be improved.

The identified component(s) or compound(s) can be any component or compound that can be indicative of a condition, disease, deficiency, etc. in a dermatological sample. The number of component(s) or compound(s) identified and/or monitored can be 1, 2, 3, 4, 5, 6, 7, 8, 9, 10, 15, 20, 50, 100 or greater. These values can define a range, such as between about 5 and 20 component(s) or compound(s). The component(s) or compound(s) that can be identified and/or monitored, or the molecules that can detected, can include, but are not limited to, urea, ureic acid, nonenals (e.g., 2-nonenal, 4-hydroxy nonenal), L-ascorbate, α-tocopherol, beta-carotene, uric acid, CoQ10, glutathione, free fatty acids (e.g., omega-3 and omega-6, C16:1 sapienic acid), oxygenated fatty acids, triglycerides, wax esters, ceramides, gangliosides, sulfatides, cholesterol, cholesterol esters, squalene, squalene hydroperoxide, endocannabinoids, eicosanoids, N-acylethanolamines (e.g., palmitoylethanolamide), etc. In some embodiment, peptides or proteins of interest can also be monitored, with or without the monitoring of smaller molecules.

The data obtained on the dermatological related compound(s), e.g., identity and intensity spectrum, can be used to classify the sample into one or more groups that can be associated with a condition or disease (e.g., dry skin, sun damaged, inflamed tissue, allergic reaction, fatty acid rich, fatty acid deficient, etc.). The identified dermatological related compound(s) can be compared to one or more known dermatological profiles. These profiles can be population based profiles that the subject's immediate profile can be compared against. The population can be the entire subject population (e.g., all humans) or sub-populations based on age, gender, ethnicity, geographical region, other, or combinations thereof. The profile can also be a personalized profile based on one or more past analyses of the same subject. The methods and the apparatus of the present disclosure can be used to monitor the treatment effects of a personalized cosmetic or treatment provided to a customer, consumer or patient to monitor its effects.

The condition, disease, deficiency etc. identified from the classification of the dermatological related compound(s) in the sample can be any dermatological related condition, disease or deficiency that can be determined by identifying or monitoring compounds or components using the methods of the present disclosure. In one embodiment, the output of the methods and apparatus of the present disclosure can be a simplified classification based on the data obtained on the dermatological related compounds, such as their correspondence to a skin/hair type or condition. The condition, disease or deficiency identified can include an indication of the skin or hair identification, the skin or hair status, an inflammatory status or a response or efficacy of a treatment(s). The condition, disease or deficiency identified can also include an indication of UV-induced photodamage, allergies, skin aging, inflammatory skin responses, dryness, dermatitis, infections, inflammatory skin conditions, atopy, acne, flea allergy dermatitis, otitis externa, as well as adverse reactions to food, including food allergy and intolerance and hair disease such as alopecia. The method of the present disclosure can also include determining a treatment or remedy, such as providing a personalized cosmetic or treatment to address the condition, disease or deficiency identified.

The method of the present disclosure can determine components and associated conditions in a dermatological sample and/or prepare personalized cosmetics or treatments in a shorter time that methodology of the prior art. The method can determine the components etc. and/or prepare a personalized cosmetic or treatment within 10 seconds, 20, 30, 40, 50 or 60 seconds, 2 minutes, 3, 4, 5, 10, 20, 30, 40, 50 or 60 minutes, or 1.5 hours, 2, 3, 4, 5, 6, 7, 8, 9, 10, 11, 12 or 24 hours. These values can also be used to define a range, such as between about 10 minutes and about 60 minutes. In one embodiment, the steps of the present disclosure can be performed in less than about 5 minutes. In another embodiment, the present disclosure can determine components and associated conditions in a dermatological sample and/or prepare personalized cosmetics or treatments without sending a sample to a laboratory for analysis. The methodology can be used as a point of care test, e.g., pharmacy, doctor's office, etc. For example, the present disclosure can be used to provide results to consumers in real-time, helping them make the best choices of consumer care products and medications.

The present disclosure can determine components and associated conditions in a dermatological sample and/or prepare personalized cosmetics or treatments without extraction, hydrolysis, filtration, derivatization, chromatographic separation (e.g., GC-FID) or combinations thereof. The prior art methodology involves one or more of these steps and can take hours to complete, e.g., at least about 2 hours. The method of the present disclosure can reduce the analysis time by about 10%, 20, 30, 40, 50, 60, 70, 80, 90, 100, 200, 300, 500, or about 1000%. These values can also be used to define a range, such as between about 20% and about 50%.

In another embodiment, the present disclosure relates to a method of providing a personalized cosmetic product to a customer, consumer, patient, etc. including receiving dermatological data from a dermatological analysis of a sample provided by the customer, obtaining ingredients for producing the personalized cosmetic product, generating a customized cosmetic product formula using the ingredients and dermatological data, and preparing the customized cosmetic product, wherein these steps can be performed in a relatively short period of time, such as less than about 30 minutes.

The personalized cosmetic product can be provided to a customer, consumer, patient, etc. by analysis of one or more of the customer, consumer, patient, etc. samples, determining an appropriate cosmetic or treatment, preparing or formulating it and supplying it to the customer, consumer, patient, etc. The dermatological data received, considered or evaluated can be the identification of one or more individual dermatological related components or compounds, the amount of one or more individual dermatological related component or compounds, including quantitative and semi-quantitative information, the classification of the dermatological related components or compounds identified and/or quantified which can be based on additional calculations of these data (e.g., groups or ratios). The dermatological data can also be received by generating sample ions from the subject's sample using a surface desorption ionization source, receiving the ions into a mass spectrometer, and identifying dermatological related compounds in the sample as provided herein.

The present disclosure can include quantification or semi-quantification using a panel of selected markers belonging to one or more chemical classes as disclosed herein. A combination of different ratios can be used to normalize sample amount and correct from individual variability. A combination of different ratios can also be used to generate a composite biomarker panel associated with predetermined consumer care products, medical treatments and nutritional interventions. Ratiometric analysis can also be used, which can be predictive of enzymatic activities by measuring the ratio or precursors versus products of enzymatic reactions. For example, stearoyl Co-A desaturase activity can be monitored by analyzing ratio of fatty acids C16:1/C16:0 (product/precursor). This measure can be related to dryness of skin. Alternatively, the ratio omega-6/omega-3 fatty acids can be used as indication of sensitivity to inflammation, and can be used to advise or notify the subject that a specific nutritional intervention or skin treatment should be avoided, such as for example, irritations and inflammations after exposure to sunlight and UV radiations.

The ingredients for producing the personalized cosmetic or treatment product can be obtained by any commercially available means and practices. The customized cosmetic or treatment product formula using the ingredients and dermatological data can be generated by standard formulation techniques and practices. The ingredients can include one or more individual dermatological related components or compounds determined to be in the sample. These components and compounds can be included in a personalized cosmetic or treatment, for example, to treat a deficiency in these components or compounds in the subject. The ingredients can also include other known components and compounds that can treat the condition, disease, etc. determined by the analysis provided herein. For example, the ingredients can include naturally occurring polypeptides (small proteins), epidermal growth factors, hyaluronic acid, etc. to stimulate collagen production in the skin wherein the sample was not monitored for collagen but the sample was classified as requiring collagen production. Similarly, the ingredients can include adenosine to stimulate, blood flow to the outer layers of skin improving damage repair and cell volume, wherein the sample was not monitored for adenosine but the sample was classified as requiring adenosine.

The amount of each ingredient can also be adjusted to address or treat the condition or disease. For example, a skin sample deficient in fatty acids, and in particular omega-3 fatty acids, can include fatty acid additives, and in particular additional omega-3 fatty acid to address the particular deficiency.

The customized cosmetic or treatment product can be prepared using standard, commercially available techniques and practices, such as those described in U.S. Pat. No. 6,516,245, the entire disclosure of which is incorporated by reference in its entirety. Providing the customized cosmetic or treatment can also be done in a relatively short period of time, or in real time. The customized cosmetic or treatment can be provided in less than about 10 seconds, 20, 30, 40, 50 or 60 seconds, 2 minutes, 3, 4, 5, 10, 20, 30, 40, 50 or 60 minutes, or 1.5 hours, 2, 3, 4, 5, 6, 7, 8, 9, 10, 11, 12 or 24 hours. These values can also be used to define a range, such as between about 20 minutes and about 60 minutes. In one embodiment, the customized cosmetic or treatment can be provided in less than about 30 minutes.

The analysis and information regarding the customized cosmetic or treatment product for each customer, consumer, patient, etc. can be saved and accessed again for subsequent use, such as to track the condition or disease and the treatments associated with the condition or disease.

The present disclosure also relates to a method of treating a dermatological condition in a subject including determining the dermatological condition in a subject by obtaining a dermatological sample of the subject, generating sample ions from the subject's sample using a surface desorption ionization source, receiving the ions into a mass spectrometer, identifying dermatological related compounds in the sample, and administering a cosmetic, supplement, food, diet or a dosage form to the subject to reduce or eliminate the dermatological condition.

The dermatological condition can be any that can be determined using the real-time analysis of the present disclosure, including photodamage, photo-aging, aging, seborrheic, dermatitis(seborrhea), acne, psoriasis, skin infections, dry skin conditions, as well as eczema and atopic dermatitis, allergic reactions, psoriasis, and ichthyosis, slap conditions and alopecia, dry hair, oily hair and damaged hair. The dermatological condition can be a measure of inflammation status, such as after surgery or pharmacological treatment. The present disclosure can be used as a diagnostic or prognostic or predictive marker of inflammation or marker of response or toxicity or exposure.

The dermatological condition can also be the degree of allergic reactions after allergens inducing substances are applied on the skin. Commonly used skin allergy tests include skin prick tests, skin injection tests and skin patch tests. The primary marker of inflammation or reaction is "redness." Skin testing usually occurs at a doctor's office and involves a nurse administering the test and a doctor interpreting the results. The interpretation is by evaluation of "redness." This test can take up to 20, 30, 40 or greater minutes to complete. Some tests detect immediate allergic reactions, which develop within minutes of exposure to an allergen. Other tests detect delayed allergic reactions, which develop over a period of several days. The present disclose can shorten the amount of time for the diagnosis by providing more specific and faster analysis.

The dermatological condition can also be related to bacterial, viral, fungal and parasitic infections, including cellulitis, impetigo, staphylococcal, Athlete's foot, yeast infections, body lice, head lice, scabies, ringworm, folliculitis, piedra, demodex folliculorum, seborrheic dermatitis and moles. For example, REIMS can be used during inspections of moles to determine whether or not they require surgical removal.

Additional dermatological conditions that can be difficult to determine by visual inspection and can benefit from the present disclosure include skin cancer, lupus, rubeola (measles), acne, Hemangioma of skin, cold sore, psoriasis, rosacea, hives, vitiligo, warts, necrotizing fasciitis, cutaneous candidiasis, carbuncle, cellulitis, hypohidrosis, impetigo, cutis laxa, decubitus ulcer, erysipelas, diaper rash, dyshidrotic eczema, canker sore, herpes stomatitis, fungal nail infection, ichthyosys vulgaris, dermatomyositis, molluscum contagiosum, ingrown nails, sebaceous cyst, seborrheic keratosis, pilonidal sinus, keloid, lichen planus, actinic keratosis, stasis dermatitis and leg ulcers, corns and calluses, eczema, tinea versicolor, pemphigoid, mouth ulcers and shingles.

In other embodiments, the present disclosure can be used for the assessment of noncancerous versus cancerous disorders of moles, assessment of psoriasis versus other rushes including dermatitis and fungal infections or allergic reactions. The method and apparatus can also be used to differentiate different skin irritations or rashes on subjects (e.g., human or animals) including fungal infections. The appropriate treatment can then be applied. The method and apparatus can also be used in combination with traditional techniques and methods to support diagnosis by primary care physicians, dermatologists and dermatopathologist.

The cosmetic, supplement, food, diet or a dosage form administered can be any that can treat, reduce or eliminate a condition identified using the real-time analysis of the present disclosure. It can be a population-based or a personalized nutritional or topical supplementation (e.g., consumer products). The customized cosmetic or treatment can include components to support skin barrier function and antioxidants. For example, the personalized cosmetic can be formulated to address inflammation and/or to nourish the skin and/or the hair.

The present disclosure can further include a chromatography separation system. The chromatographic separation system can be a liquid, gas or supercritical fluid chromatographic system. The chromatographic separation system can be coupled with the desorption ionization source, in particular an atmospheric pressure ionization sources (e.g., ESI, atmospheric pressure chemical ionization, atmospheric pressure photoionization) to provide an additional separation dimension and enhanced selectivity to identify and monitor additional components and compounds.

In another embodiment, the present disclosure relates to a method of determining the spatial distribution of dermatological related compounds and components on a sample surface including generating sample ions from a first location on a sample containing dermatological related compounds and components using an ionizing source, receiving the ions into a mass spectrometer, determining the dermatological related compounds and components present in the sample at the first location, and repeating these steps on a plurality of locations. The dermatological related compounds and components can also be determined in the sample at each location.

The first location on a sample surface can be any location. The additional locations on the sample surface, e.g., the plurality of locations, can be any other locations on the sample surface. In one embodiment, the locations are all separate locations on the sample surface. The analysis at each location can be performed by either direct sampling from the sample surface by the desorption ionization source, or from samples removed from the plurality of locations.

The distance between adjacent locations can vary based on the level of detail and resolution desired for the spatial distribution analysis. To provide sufficiently detailed spatial distribution analysis, the average distance between adjacent locations can be less than about 100 mm, 90, 80, 70, 60, 50, 40, 30, 20, 10, 50, 20, 1, or about 0.5 mm. These values can also be used to define a range, such as between about 10 and 1 mm.

Figure 5:
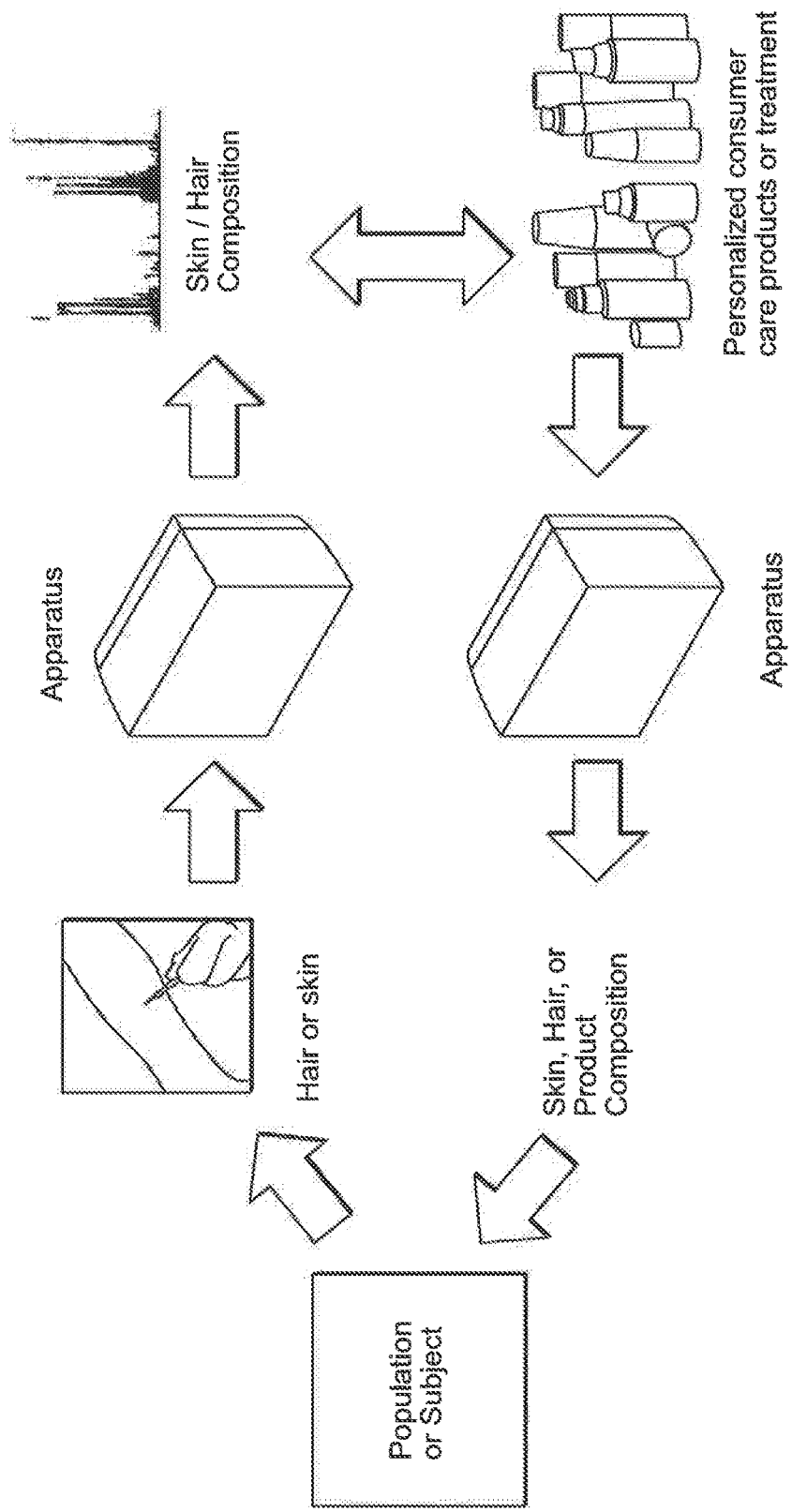
FIG. 5 shows an exemplary illustration of dermatological screening. For example, individuals can have a sample taken, e.g., skin or hair, and have it screened using a fast and simple diagnostic tool ("apparatus"), e.g., surface desorption ionization-mass spectrometry as described herein, to determine the composition of the sample and whether the individual suffers from any condition, disorder or imbalance. The individual can be treated with a cosmetic product, a supplement, a food/diet or dosage form to change or correct the condition, disorder or imbalance. The individual can be regularly re-screened to monitor the effects the cosmetic or treatment. Samples can also be held with a variety of different modules situated between the source and the mass spectrometer. The different modules can include an X-Z transmission module, tweezers, and a capillary tube.

The present disclosure also relates to a diagnostic test or screening method to determine dermatological related compounds and components in a subject (e.g., skin, hair, etc.). The analysis of dermatological related compounds and components can be used by the person, a medical professional, etc. to devise a treatment plan to correct or adjust any determined condition or disease. See FIG. 5. The therapy or treatment can include providing or administering a cosmetic, treatment, supplement or food/diet to adjust the analysis of dermatological related compounds and components to a pre-determined value or to adjust the value to a newer value that is about 5%, 10%, 20%, 30%, 40% or about 50% greater or less than originally determined. For example, a skin sample is determined to be deficient in fatty acids, and in particular omega-3 fatty acid. The therapy or treatment can provide fatty acids, and in particular omega-3 fatty acid, to ameliorate the deficiency.

The disclosures of all cited references including publications, patents, and patent applications are expressly incorporated herein by reference in their entirety.

When an amount, concentration, or other value or parameter is given as either a range, preferred range, or a list of upper preferable values and lower preferable values, this is to be understood as specifically disclosing all ranges formed from any pair of any upper range limit or preferred value and any lower range limit or preferred value, regardless of whether ranges are separately disclosed. Where a range of numerical values is recited herein, unless otherwise stated, the range is intended to include the endpoints thereof, and all integers and fractions within the range. It is not intended that the scope of the invention be limited to the specific values recited when defining a range.

The present invention is further defined in the following Examples. It should be understood that these Examples, while indicating preferred embodiments of the invention, are given by way of illustration only.

EXAMPLES

Example 1

Figure 7B:
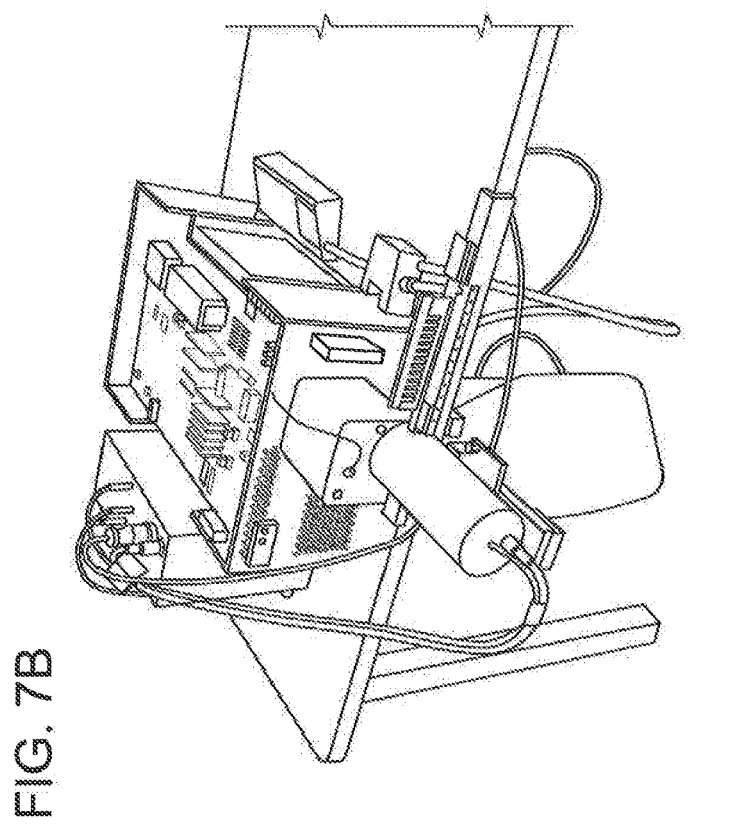
FIGS. 7A and 7B show two exemplary portable, small, real-time analysis systems of the present disclosure, both using direct-analysis in real time and a single quadrupole mass spectrometer.
Figure 7A:
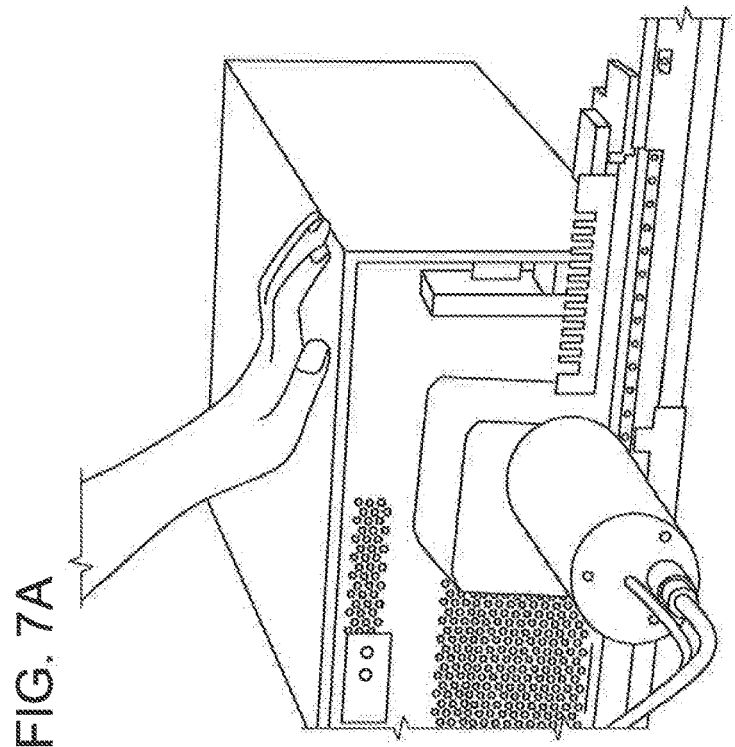

A portable, small system for real-time analysis of dermatological samples was prepared. The system includes surface desorption ionization, e.g., direct analysis in real time, coupled to a single quadrupole mass spectrometer, e.g., Acquity® QDa® Mass Detector. FIG. 7 shows two pictures of the portable, small, real-time analysis system. The portable, small design allows the system to be a customer service or point of care device (e.g., for use in stores, customer self-service stations, doctor's office, clinics, pharmacies, wellness centers, laboratories).

Dermatological compounds in a sample are analyzed using a single quadrupole mass spectrometer equipped with direct analysis in real time desorption ionization source. No chromatographic separation is required. Skin samples are tested by placing a small skin biopsy on the direct analysis in real time interface with the single quadrupole mass spectrometer. The sample can be obtained using any standard sampling technique. Twelve samples, from the same subject or from different subjects, can be collected and placed on individual spots on the card with no cross-contamination. The twelve sample positions are loaded manually (can also be done automatically) including standards for quantitation.

The analyses are conducted using a direct analysis in real time (DART®, IonSense, MA, USA) source coupled with a single quadrupole mass spectrometer (Acquity® QDa®, Waters Corporation, Milford, Mass., USA). The acquisition time is about 5-10 seconds, Ionization DART® +ve and −ve; Cone voltage 20.0 V; Source temp. 120.0° C.; DART® temp. 50 to 450° C.

A complete dermatological profile is provided in real time, without sample preparation. A bioinformatics solution is used to translate the intensity ratios in health status and well-being measures and generate reports associated with dermatological and cosmetic recommendations.

What is claimed is:

1. A method of analyzing a dermatological sample comprising:
   (i) generating sample ions directly from the dermatological sample using a surface desorption ionization source operating at or near atmospheric pressure;
   (ii) receiving the ions into a mass spectrometer;
   (iii) identifying at least one dermatological related compound in the sample from results from the mass spectrometer;
   (iv) comparing the at least one identified dermatological related compound in the sample to one or more known dermatological profiles; and
   (v) identifying at least one condition related to the dermatological sample from the comparison of the at least one identified dermatological related compound to the one or more known dermatological profiles.

2. The method of claim 1 wherein the dermatological sample is skin, hair, or a secretion.

3. The method of claim 1 wherein the dermatological sample is obtained from a subject.

4. The method of claim 3 wherein the sample ions are generated in situ directly from the subject.

5. The method of claim 1 wherein the surface desorption ionization source operates by a technique selected from the group consisting of atmospheric solid analysis probe, direct analysis in real time, rapid evaporative ionization mass spectrometry, or desorption electrospray ionization.

6. The method of claim 1, wherein the mass spectrometer is a quadrupole mass spectrometer, a time of flight mass spectrometer, or an ion trap mass spectrometer.

7. The method of claim 1 wherein steps (i)-(v) are performed in less than 5 minutes.

8. The method of claim 1 wherein the dermatological related compound is selected from the group consisting of urea, ureic acid, nonenals, L-ascorbate, α-tocopherol, beta-carotene, uric acid, CoQ10, glutathione free fatty acids, oxygenated fatty acids, triglycerides, wax esters, ceramides, gangliosides, sulfatides, cholesterol, cholesterol esters, squalene and squalene hydroperoxide, endocannabinoids and N-acyletahnolamines.

9. The method of claim 1 wherein the one or more known dermatological profiles is generated from the same subject.

10. The method of claim 9 further comprising determining a treatment or remedy.

11. A method of providing a personalized cosmetic product to a customer, comprising:
   (i) receiving dermatological data from a dermatological analysis of a sample provided by the customer,
   (ii) obtaining ingredients for producing the personalized cosmetic product;
   (iii) generating a customized cosmetic product formula using the ingredients and dermatological data; and
   (iv) preparing the customized cosmetic product;
wherein:
   steps (i) (iv) are performed in less than 30 minutes; and
   the dermatological data is received by:
      (a) generating sample ions directly from the customer's sample using a surface desorption ionization source operated at or near atmospheric pressure;
      (b) receiving the ions into a mass spectrometer; and (c) identifying at least one dermatological related compound in the sample from the results from the mass spectrometer.

12. The method of claim 11 further comprising saving the dermatological data from the customer for subsequent use.

13. The method of claim 11 wherein the dermatological sample is skin, hair, or a secretion.

14. The method of claim 11 wherein the surface desorption ionization source operates by a technique selected from the group consisting of atmospheric solid analysis probe, direct analysis in real time, rapid evaporative ionization mass spectrometry, or desorption electrospray ionization.

15. The method of claim 11, wherein the mass spectrometer is a quadrupole mass spectrometer, a time of flight mass spectrometer, or an ion trap mass spectrometer.

16. A method of treating a dermatological condition in the subject comprising:
(i) determining the dermatological condition in a subject by
(a) obtaining a dermatological sample from the subject;
(b) generating sample ions directly from the subject's sample using a surface desorption ionization source operated at or near atmospheric conditions;
(c) receiving the ions into a mass spectrometer;
(d) identifying at least one dermatological related compound in the sample from results from the mass spectrometer; and
(ii) administering a cosmetic, supplement, food, diet or a dosage form to the subject to reduce or eliminate the dermatological condition.

17. The method of claim 16 wherein the surface desorption ionization source operates by a technique selected from the group consisting of atmospheric solid analysis probe, direct analysis in real time, rapid evaporative ionization mass spectrometry, or desorption electrospray ionization.

18. The method of claim 16 wherein the dermatological sample is skin, hair, or a secretion.

19. The method of claim 16, wherein the mass spectrometer is a quadrupole mass spectrometer, a time of flight mass spectrometer, or an ion trap mass spectrometer.

* * * * *